US008821406B2

(12) United States Patent
Callister et al.

(10) Patent No.: US 8,821,406 B2
(45) Date of Patent: *Sep. 2, 2014

(54) VASCULAR INTRODUCER WITH TEMPERATURE MONITORING PROBE AND SYSTEMS FOR ENDOVASCULAR TEMPERATURE CONTROL

(75) Inventors: Jeffrey P. Callister, Redwood City, CA (US); Michael W. Dae, Belmont, CA (US); Amy L. Hammack, San Mateo, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 74 days.

This patent is subject to a terminal disclaimer.

(21) Appl. No.: 13/115,000

(22) Filed: May 24, 2011

(65) Prior Publication Data

US 2011/0288432 A1 Nov. 24, 2011

Related U.S. Application Data

(63) Continuation of application No. 10/238,925, filed on Sep. 10, 2002, now Pat. No. 7,186,222, and a continuation of application No. 11/709,108, filed on Feb. 20, 2007, now Pat. No. 7,946,996.

(51) Int. Cl.
  *A61B 5/00* (2006.01)
(52) U.S. Cl.
  USPC .......................................... 600/549; 600/526
(58) Field of Classification Search
  USPC ................................................ 600/549, 526
  See application file for complete search history.

(56) References Cited

U.S. PATENT DOCUMENTS

| 2,012,112 | A |   | 8/1935  | States              |         |
|-----------|---|---|---------|---------------------|---------|
| 2,816,997 | A |   | 12/1957 | Conrad              |         |
| 3,726,269 | A |   | 4/1973  | Webster, Jr.        |         |
| 3,951,136 | A |   | 4/1976  | Wall                |         |
| 3,995,623 | A |   | 12/1976 | Blake et al.        |         |
| 4,176,660 | A |   | 12/1979 | Mylrea et al.       |         |
| 4,417,886 | A | * | 11/1983 | Frankhouser et al.  | 604/510 |
| 4,419,999 | A |   | 12/1983 | May, Jr. et al.     |         |
| 4,476,872 | A |   | 10/1984 | Perlin              |         |
| 4,508,123 | A |   | 4/1985  | Wyatt et al.        |         |
| 4,633,885 | A |   | 1/1987  | DuBrucq et al.      |         |
| 4,650,472 | A | * | 3/1987  | Bates               | 604/158 |
| 4,796,640 | A |   | 1/1989  | Webler              |         |
| 4,886,506 | A |   | 12/1989 | Lovgren et al.      |         |
| 4,941,475 | A |   | 7/1990  | Williams et al.     |         |

(Continued)

OTHER PUBLICATIONS

"The Subclavian Vein", Central Venous Access and Monitoring. Update in Anaesthesia, Issue 12 (2000) Article 13. http://www.nda.ox.ac.uk/wfsa/html/u1213_03.htm.

(Continued)

*Primary Examiner* — Navin Natnithithadha
*Assistant Examiner* — Etsub Berhanu
(74) *Attorney, Agent, or Firm* — Robert D. Buyan; Stout, Uxa & Buyan, LLP

(57) ABSTRACT

An introducer sheath/temperature probe assembly that is insertable into a blood vessel of a human or veterinary patent to measure the temperature of blood flowing through that blood vessel. The introducer sheath/temperature probe assembly may be used in conjunction with an indwelling heat exchange catheter system to warm or cool all or a portion of the patient's body to a desired target temperature and to maintain such target temperature for a desired period of time.

5 Claims, 7 Drawing Sheets

(56) References Cited

U.S. PATENT DOCUMENTS

| | | |
|---|---|---|
| 4,950,257 A | 8/1990 | Hibbs et al. |
| 5,059,186 A * | 10/1991 | Yamamoto et al. ............ 604/537 |
| 5,174,285 A | 12/1992 | Fontenot |
| 5,211,631 A | 5/1993 | Sheaff |
| 5,254,097 A | 10/1993 | Schock et al. |
| 5,271,410 A | 12/1993 | Wolzinger et al. |
| 5,334,160 A | 8/1994 | Ellis |
| 5,486,208 A | 1/1996 | Ginsburg |
| 5,573,007 A | 11/1996 | Bobo, Sr. |
| 5,588,438 A | 12/1996 | McKown et al. |
| 5,713,371 A | 2/1998 | Sherman et al. |
| 5,807,269 A | 9/1998 | Quinn et al. |
| 5,837,003 A | 11/1998 | Ginsburg |
| 5,984,879 A | 11/1999 | Wallace et al. |
| 6,126,684 A | 10/2000 | Gobin et al. |
| 6,146,411 A | 11/2000 | Noda et al. |
| 6,149,673 A | 11/2000 | Ginsburg |
| 6,231,594 B1 | 5/2001 | Dae |
| 6,264,679 B1 | 7/2001 | Keller et al. |
| 6,290,717 B1 | 9/2001 | Philips |
| 6,299,599 B1 | 10/2001 | Pham et al. |
| 6,383,144 B1 | 5/2002 | Mooney et al. |
| 6,419,643 B1 | 7/2002 | Shimada et al. |
| 6,454,792 B1 | 9/2002 | Noda et al. |
| 6,575,623 B2 | 6/2003 | Werneth |
| 6,592,544 B1 | 7/2003 | Mooney et al. |
| 6,602,243 B2 | 8/2003 | Noda |
| 6,607,517 B1 | 8/2003 | Dae et al. |
| 6,652,565 B1 | 11/2003 | Shimada et al. |
| 6,866,638 B2 | 3/2005 | Dae et al. |
| 7,186,222 B1 | 3/2007 | Callister et al. |
| 7,946,996 B2 | 5/2011 | Callister et al. |

OTHER PUBLICATIONS

USPTO Office Action dated Jun. 18, 2004 in related U.S. Appl. No. 10/238,925, filed Sep. 10, 2002.

USPTO Office Action dated Apr. 20, 2005 in related U.S. Appl. No. 10/238,925, filed Sep. 10, 2002.

USPTO Office Action dated Nov. 2, 2005 in related U.S. Appl. No. 10/238,925, filed Sep. 10, 2002.

USPTO Office Action dated Jul. 21, 2006 in related U.S. Appl. No. 10/238,925, filed Sep. 10, 2002.

USPTO Office Action dated Mar. 5, 2009 in related U.S. Appl. No. 11/709,108, filed Feb. 20, 2007.

USPTO Office Action dated Sep. 29, 2009 in related U.S. Appl. No. 11/709,108, filed Feb. 20, 2007.

USPTO Office Action dated Jun. 24, 2010 in related U.S. Appl. No. 11/709,108, filed Feb. 20, 2007.

* cited by examiner

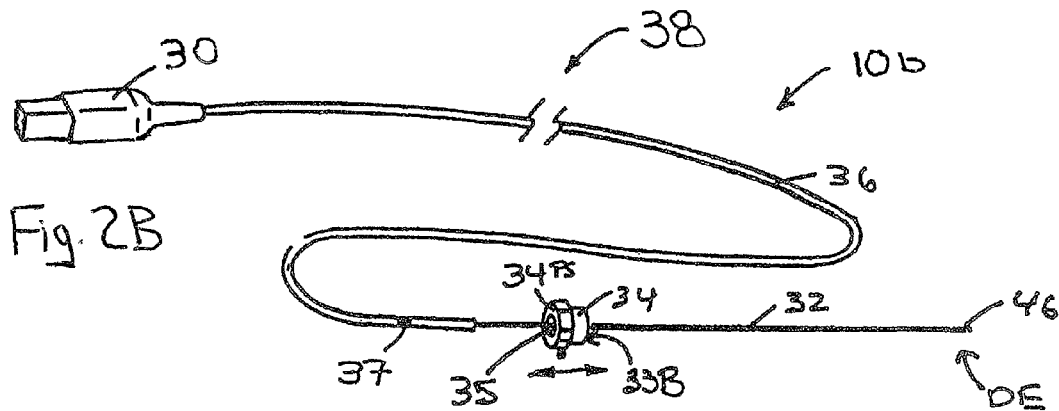
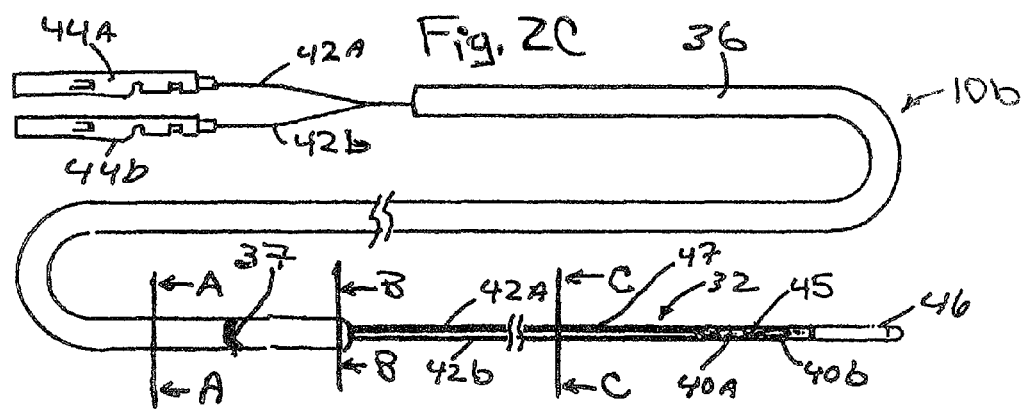
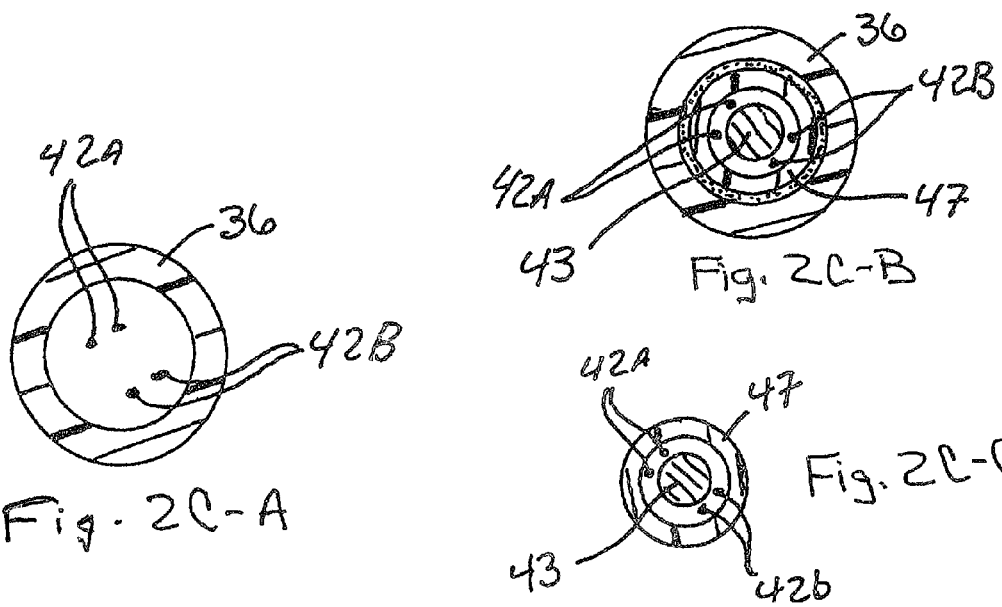

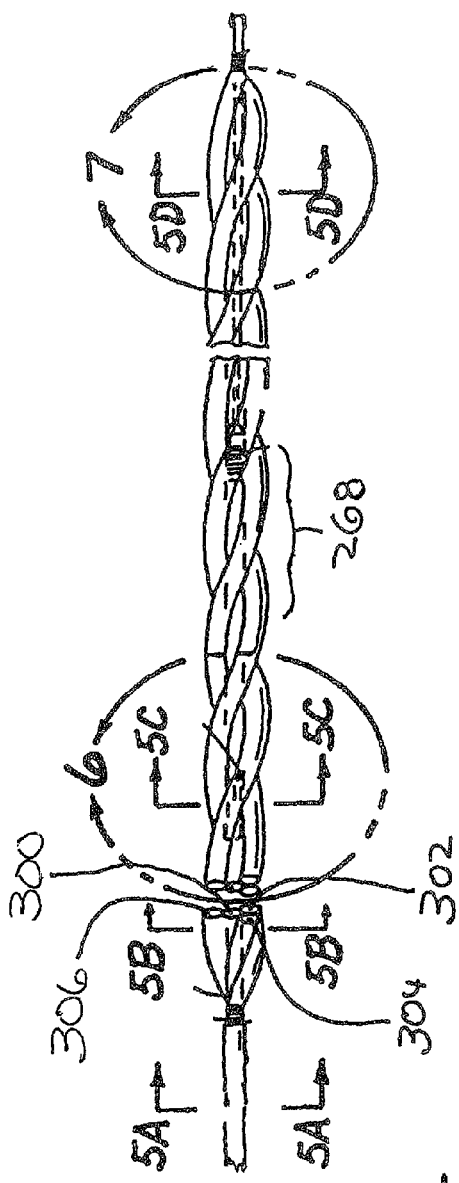
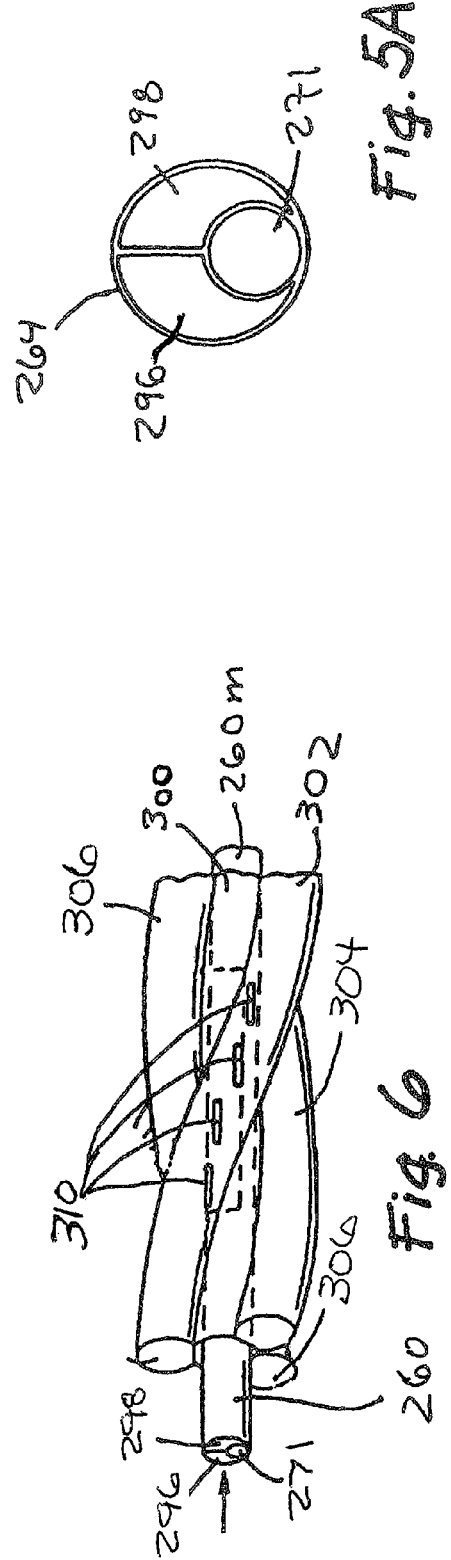
Fig. 5
Fig. 5A
Fig. 6

VASCULAR INTRODUCER WITH TEMPERATURE MONITORING PROBE AND SYSTEMS FOR ENDOVASCULAR TEMPERATURE CONTROL

RELATED APPLICATION

This application is a continuation of U.S. application Ser. No. 11/709,108 filed Feb. 20, 2007 and issued as U.S. Pat. No. 7,946,996 on May 24, 2011, which is a continuation of U.S. patent application Ser. No. 10/238,925 filed Sep. 10, 2002 and issued as U.S. Pat. No. 7,186,222 on Mar. 6, 2007, the entire disclosure of each such prior application being expressly incorporated herein by reference.

FIELD OF THE INVENTION

This invention relates generally to devices and methods for medical treatment and more particularly to devices and methods for monitoring body temperature and for effecting control of body temperature.

BACKGROUND OF THE INVENTION

In the practice of clinical medicine and surgery, numerous situations arise in which it is desirable to determine or monitor the core body temperature of a human or veterinary patient. Various devices have heretofore been proposed for use in measuring or monitoring core body temperature, including intravascular thermistors or temperature probes that may be inserted into blood vessels to measure or monitor the temperature of blood flowing through such blood vessels.

In recent years, endovascular heat exchange catheters and related apparatus have been developed for heating or cooling the bodies of patients and/or for maintaining the patient's core body temperature within a desired temperature range. Examples of such endovascular heat exchange catheters and related apparatus include those described in U.S. Pat. No. 5,486,208 (Ginsburg), PCT International Publication WO 00/10494 (Machold et al.), U.S. Pat. No. 6,264,679 (Keller et al.), PCT International Publication Nos. WO-00/10494 (Radiant Medical, Inc.) and WO 01/58397 (Radiant Medical, Inc.), all of which are expressly incorporated herein by reference.

In some instances, the core body temperature of the patient is monitored and such monitored core body temperature is used as a basis for feedback control of the heat exchange catheter so as to maintain the patient's body temperature within a pre-set or desired temperature range. Examples of such feedback control systems are described and/or claimed in U.S. Pat. Nos. 5,837,003 (Ginsburg) and 6,149,673 (Ginsburg) and PCT International Patent Publication No. WO-00/10494 (Radiant Medical, Inc.), which are expressly incorporated herein by reference.

Although the prior art has included various types of indwelling temperature measuring devices, none of those prior art devices are believed to be optimally designed for use in all patients and all clinical conditions. Specifically, there exists a need in the art for an introduce sheath/temperature probe assembly whereby a tubular introducer sheath may be inserted into a blood vessel and a temperature measuring probe may be inserted through that introducer sheath for the purpose of measuring or monitoring the temperature of the patient's blood flowing through the blood vessel into which the introducer sheath is inserted.

SUMMARY OF THE INVENTION

The present invention provides an introducer sheath/temperature probe assembly for measuring the blood temperature of a human or veterinary patient. The introducer sheath/temperature probe assembly comprises a) a tubular introducer sheath that is insertable into a blood vessel and b) a temperature measuring probe that is insertable into the lumen of the introducer sheath. When the temperature probe is inserted into the lumen of the introducer sheath, one or more temperature sensors (e.g., thermistors) mounted on or in the temperature probe will sense the temperature of the patient's blood flowing through the blood vessel into which the introducer sheath is inserted. An atraumatic tip member may be formed on or attached to the distal end of the temperature probe and such atraumatic tip member may be allowed to protrude beyond the distal end of the introducer sheath to deter trauma or injury to the inner surface of the blood vessel wall. The temperature probe may include a single temperature sensor or a plurality of temperature sensors to provide one or more signals indicative of the blood temperature. In use, when the probe is deployed through the introducer, the probe may be positioned so that the atraumatic tip is extending out the distal end of the introducer sheath and the sensor or sensors may be located within the introducer sheath.

If there are more than one sensor, they may be placed side-by side in the probe or may be longitudinally arranged. Also in cases where two or more temperature sensors are included in or on the probe, such temperature signals may be checked against one another to ensure accuracy of the temperature measurement. If the difference between the temperature measured by the multiple sensors is less than a maximum allowable differences, the temperatures measured by the sensors may be averaged to arrive at a current sensed temperature. Alternatively, one of the sensors may be predesignated as the "driver" sensor and the signal from that sensor may be the temperature signal that is used by the controller as the patient temperature. In yet another embodiment, the two or more temperature signals may be checked against each other and if the difference is within the acceptable limit, the controller may select which signal to use as the representative signal of the patient temperature. For example, if the controller is cooling the patient, the controller may select the cooler of two signals to avoid over cooling the patient, or if the patient is warming, the controller may select the warmer of two signals to avoid over warming the patient. On the other hand, if the temperatures measured by the sensors differ by more than a maximum allowable temperature difference, such may be taken as an indication of a sensor malfunction or inaccurate measurement and an alarm may be provided to the operator or the entire system may be shut down.

Further in accordance with the present invention, there is provided a body temperature control system which comprises an introducer sheath/temperature probe assembly of the foregoing character further in combination with a heat exchange catheter that is insertable into the patient's vasculature to heat and/or cool the patient's blood. In this body temperature control system, the current body temperature measured by the temperature probe may be utilized as a basis for feedback control of the heat exchange catheter to warm or cool the patient's body to a desired target temperature and to thereafter maintain the patient's body at or near the desired target temperature for a desired period of time.

Further in accordance with this invention, a method is provided for determining the core body temperature by obtaining a temperature signal from a temperature probe within an introducer sheath located within one of the great veins, e.g. the inferior vena cava, the superior vena cava, the right and left femoral veins, the subclavian veins and the jugular veins.

Further aspects and advantages of the present invention will be recognized and understood by those of skill in the art upon reading of the detailed description and examples of the invention set forth herebelow and in the accompanying drawings.

DETAILED DESCRIPTION OF THE DRAWINGS

FIG. 2B is a perspective view of a temperature probe component of the introducer sheath/temperature probe assembly of FIG. 1.

FIG. 2C is a partial cut away view of the temperature probe component of FIG. 2B.

FIG. 5 is a side elevational view of the heat exchange catheter component of the automated endovascular heat exchange system of FIG. 4.

FIG. 5A is a cross-sectional view through line 5A-5A of FIG. 5.

FIG. 6 is an enlarged, perspective view of the portion of the heat exchange catheter within circle 6 of FIG. 5.

DETAILED DESCRIPTION

A. An Introducer Sheath/Temperature Probe Assembly and its Method of Use

FIGS. 1 and 2B through 2C and 2C-A through 2C-C show an example of an introducer sheath/temperature probe assembly 10 of the present invention. This assembly 10 comprises an introducer sheath component 10A and a temperature probe component 10B.

Figure 2A:
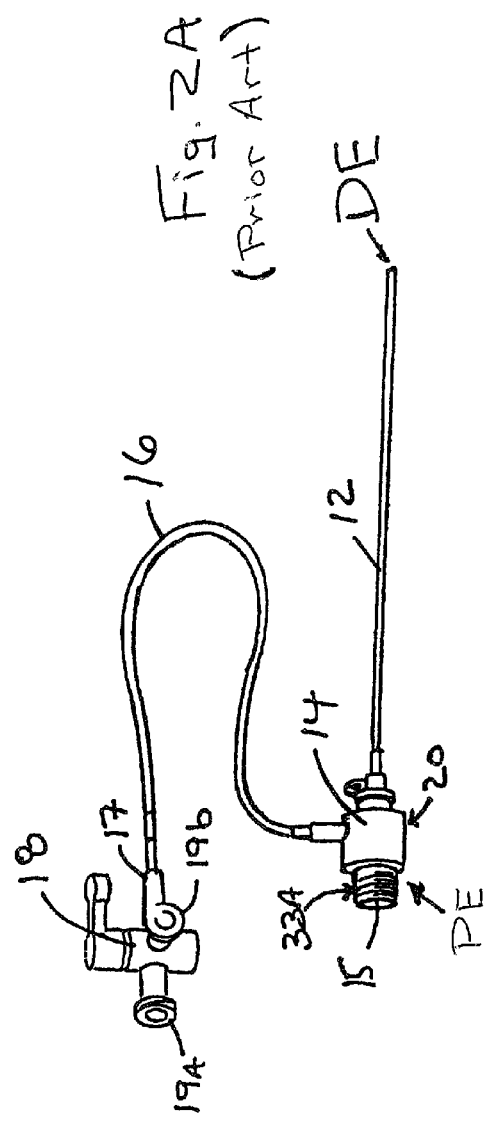
FIG. 2A is a perspective view of the introducer sheath component of the introducer sheath/temperature probe assembly of FIG. 1.

The introducer sheath component 10A, as shown in FIG. 2A, comprises an introducer cannula 12 which has a distal end DE and a proximal end PE. A hub 14 is attached to the proximal end of the introducer cannula. An engagement surface 33A, such as a helical thread is formed on the outer aspect of the proximal portion of the introducer hub 14. A hollow bore (not shown) extends longitudinally through the hub 14 from an opening 15 formed in the proximal end of the hub 14 into the lumen (not shown) of the cannula 12. A hemostatic valve 20 (not visible on figures), such as a duck bill valve, is mounted within the bore of the hub 14 to prevent blood from back-flowing out of the proximal opening 15 when the cannula 12 is inserted into a blood vessel. A side tube 16 extends from the side of the hub 14 to permit infusion of fluids or substances into the bore of the hub 14 and through the lumen of the cannula 12. One arm 17 of a three-way stopcock 18 is attached to the proximal end of the side tube 15. The other arms 19a, 19b of the stopcock 18 are in the form of Luer fittings so as to facilitate the connection of syringes and/or solution administration tubes to the stopcock 18, as is well known in the art. If any injection of medicaments or other substance is made through the side arm while the probe is in the introducer at temperatures other than blood temperature, it will be recognized that this will affect the temperature signal sent by the sensors in the probe. Further, the probe is generally relatively snug within the introducer, and therefore there would be little room for infusion through the introducer with the probe in place. For these reasons, the use of the side arm will often require the suspension of taking temperature signals for a period of time after the infusion, and may require the removal of the probe from the introducer for a period of time to facilitate the injection through the side arm.

Figure 4:
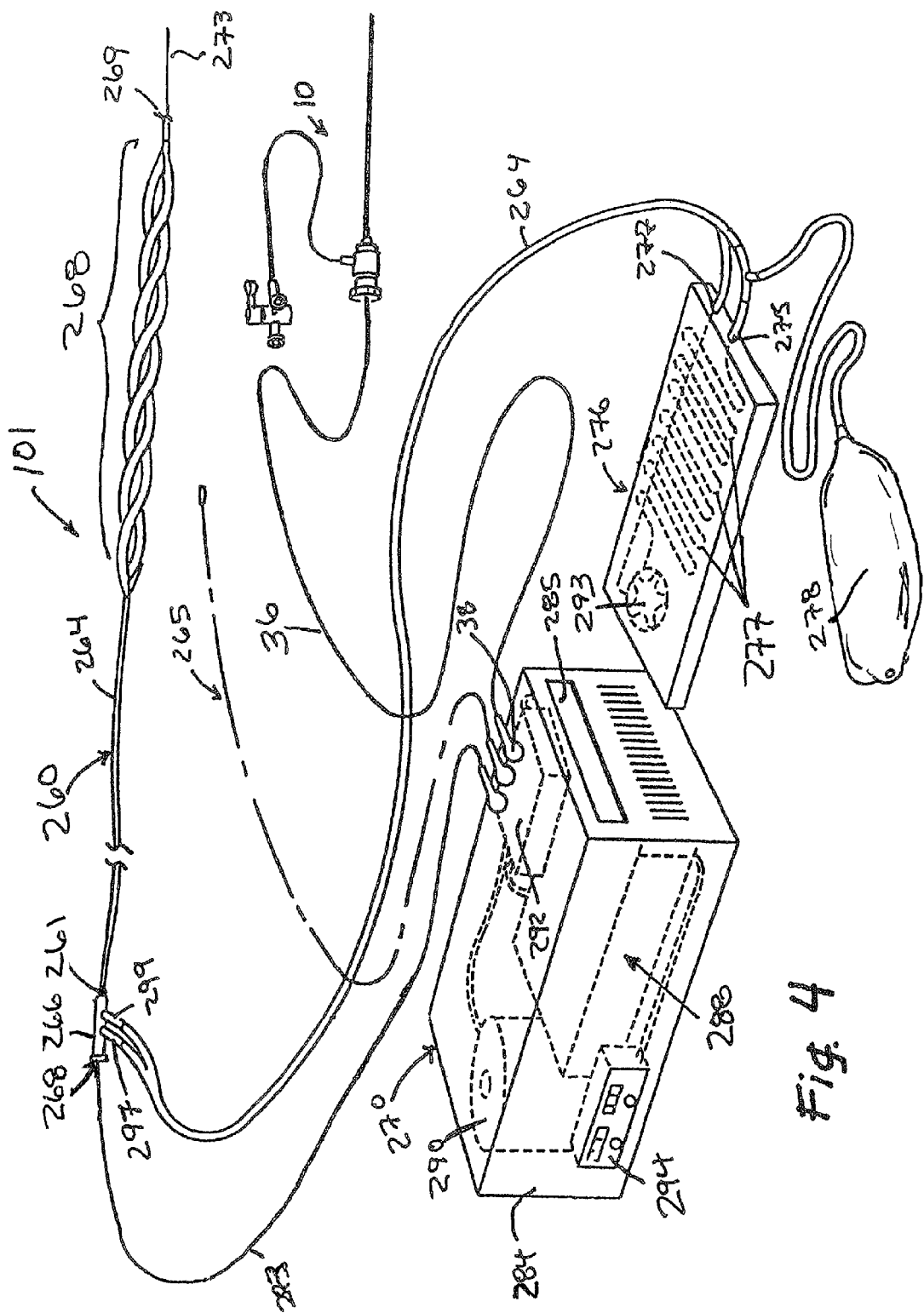
FIG. 4 is a perspective view of one type of automated endovascular heat exchange system incorporating an introducer sheath/temperature probe assembly of the present invention.

The temperature probe component 10B, as shown in FIGS. 2B and 2C, comprises an elongate temperature probe 32 that is sized for insertion through the proximal opening 15 of the introducer hub 14, through the hemostatic valve 20 and through the lumen of the introducer cannula 12. First and second temperature sensors 40A, 40B are positioned within the elongate probe 32. These temperature sensors 40A, 40B are connected by wire pairs 42A, 42B to female connectors 44A, 44B. The wire pairs 42A, 42B extend through cable 36 and the female connectors 44A, 44B are positioned within plug 38 to facilitate connection to corresponding male connectors on the controller 292 of heater/cooler/control unit 270, as shown in FIG. 4. A concave cap member 34 having an engagement surface 33B such as a helical thread formed on its inner aspect is provided as part of the introducer assembly and the probe 32 extends through a sealed opening in the center of the cap member 34.

Figure 5B:
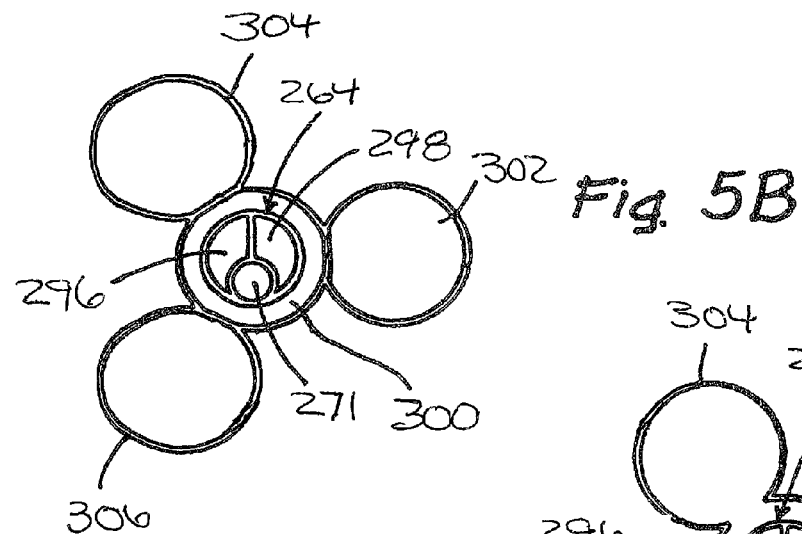
FIG. 5B is a cross-sectional view through line 5B-5B of FIG. 5.
Figure 5C:
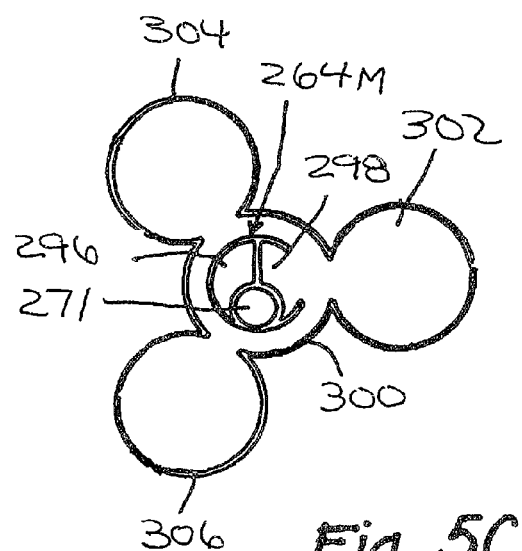
FIG. 5C is a cross-sectional view through line 5C-5C of FIG. 5.

With particular reference to the cross sections shown in FIGS. 5C-A, 5C-B and 5C-C, the temperature probe component 10B may be constructed by first attaching the atraumatic distal tip member 46 to the distal end of a plastic tube 47. The temperature sensors 40A, 40B (e.g., thermistors) are attached by way of a glue, adhesive, weldment or other suitable means, to the distal portion of a rigid stylet 43 (such as a solid metal rod). A quantity of ultraviolet (UV) curable adhesive is placed within the distal end of the tube 47, just proximal to the previously attached atraumatic tip member 46. The wire pairs 42A, 42B are then drawn taut along side of the stylet 43 to which the sensors 40A, 40B had been attached and the stylet 43 is then inserted into the tube 47 such that the distal end of the stylet 43 and the sensors 40A, 40B become immersed within the quantity of ultraviolet (UV) curable adhesive that had been placed within the distal end of the tube 47. Thereafter, a UV light is shone through the wall of the tube 47 to cure the adhesive, thereby securing the stylet 43, sensors 40A, 40B within the tube 47. The proximal segments of the wire pairs 42A, 42B are then drawn through the lumen of flexible tube 36 and the proximal end of tube 47 containing stylet 43 is received within and secured (e.g., by adhesive) to the distal end of the flexible tube 36, as shown in FIGS. 2C and 2C-B. Plug connectors 44A,44B are then connected to the proximal ends of the wire pairs 42A, 42B that extend out of the distal end of the flexible tube 36 and such plug connectors are inserted within plug housing 38, thus completing the construction of the temperature probe assembly 10B.

Figure 1:
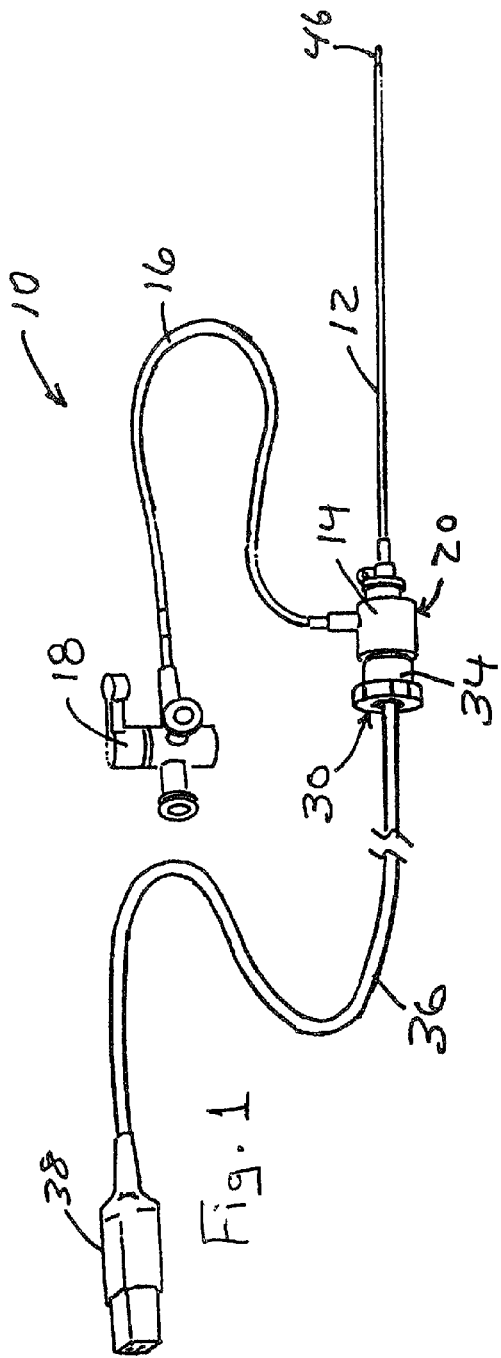
FIG. 1 is a perspective view of one embodiment of an introducer sheath/temperature probe assembly of the present invention.

When the temperature probe 32 is inserted through the proximal opening 15 of the introducer hub 14, through the hemostatic valve 20 and through the lumen of the introducer cannula to its operative position within the introducer cannula 12, the cap member 34 may be screwed onto the proximal end of the introducer hub 15 such that the engagement surfaces 33A and 33B engage one another and hold the cap member 34 on the introducer hub 14. A gripping member 35, such as a compressible 0-ring or Tui Borst valve having an opening of variable diameter may be mounted within the cap member 34 such that the probe 32 extends through a central opening within the gripping member 34. As the cap member 34 is advanced and tightened (e.g, screwed onto) the proximal aspect of the introducer hub 14 as shown in FIG. 1, the gripping member 30 will constrict about the temperature probe 34, thereby forming a seal and holding the probe 34 in substantially fixed longitudinal position within the introducer cannula 12. In the particular example shown in these drawings, an atraumatic tip member 46 is attached to or formed on the distal end of the temperature probe 32 and the temperature probe 32 is held in a position whereby all or a substantial portion of the atraumatic tip member 46 protrudes out of and beyond the distal end DE of the introducer cannula 12. The sensors 40A, 40B may reside just within the introducer cannula, and the atraumatic tip 46 of the probe is all that protrudes out of the distal end DE of the introducer cannula. It has been found that even if the sensors do not exit the cannula and reside directly in the bloodstream, they none-the-less sense an accurate temperature of the bloodstream. This has been found to be true when the core body temperature is static, or even if the core body temperature is changing, as when an endovascular temperature system is operating to cool a patient described below. The sensors themselves may be rather stiff and thus are less traumatic to the vessel if they remain in the introducer sheath. By the same token, the distal end DE of the introducer sheath is less traumatic if there is a soft extension which tapers gently down extending out of the blunt end of the tube itself. Thus it may be advantageous to place the probe 32 within the introducer cannula 12 so that the introducer cannula 12 surrounds and protects the sensors 40A, 40B but such that the atraumatic distal tip 46 protrudes out of and beyond the distal end of the introducer cannula 12. The distal tip may be coated with a lubricious coating to enhance ease of insertion and to increase the atraumatic nature of the tip with the vessel wall. A coating which is both anti-thrombogenic and lubricious is highly advantageous since it would simultaneously aid the probe in being non-thrombogenetic and increase the atraumatic nature of the tip.

The length, diameter and relative stiffness of the introducer cannula 12, probe 32 and the probe's atraumatic tip member 46 may vary, depending on the type and size of blood vessel into which the assembly 10 is to be inserted. In applications wherein the assembly 10 is to be inserted into a femoral vein or femoral artery, the introducer cannula will preferably be 7.5-14 cm in length, 2 French to 6 French in inner diameter and may be made of high density polyethylene or other suitable material having a Durometer hardness of about 72D, and the probe 32 will preferably be of a length and diameter that allows it to fit snugly but slidably within the lumen of the introducer cannula 12. In such femoral embodiments, the probe's atraumatic tip member 46 will preferably be approximately 5 cm in length and will be made of material having a Durometer hardness of 25D-35D and configured to minimize trauma to the blood vessel wall (e.g., having a rounded, blunt distal tip). It is preferable that all or substantially all of the atraumatic tip member 46 protrude beyond the distal end DE of the cannula 12. The temperature sensors 40A, 40B are preferably positioned on or in the probe 32 proximal to the atraumatic tip member 46 and are housed within the cannula 21 when the probe 32 is fully advanced to its operative position with its atraumatic distal tip member 46 protruding out of the distal end of the cannula 12. To facilitate such positioning of the temperature probe 32 within the lumen of the introducer cannula 12, a mark 37 may be formed on the tube 36 such that the temperature probe 32 may be advanced into the cannula 12 until the mark 37 is at a predetermined location relative to the cap member 34 (e.g., where the mark 37 if immediately adjacent to the flat proximal surface 34PS of the cap member 34) and the cap member 34 may then be tightened, thereby holding the probe 32 within the cannula 12 in a position where the atraumatic tip member 46 protrudes out of the distal end of the cannula 12 but the probe's sensors 42A, 42B remain positioned within the cannula 12.

Figure 3A:
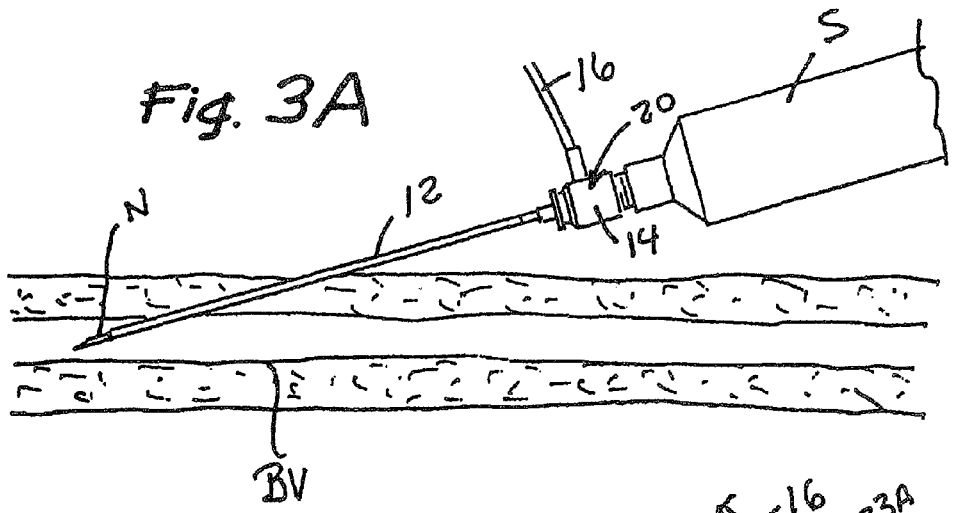
FIGS. 3A-3C show in step-by-step fashion a presently preferred method for insertion of an introducer sheath/temperature probe assembly of the present invention into a blood vessel of a human or veterinary patient.
Figure 3B:
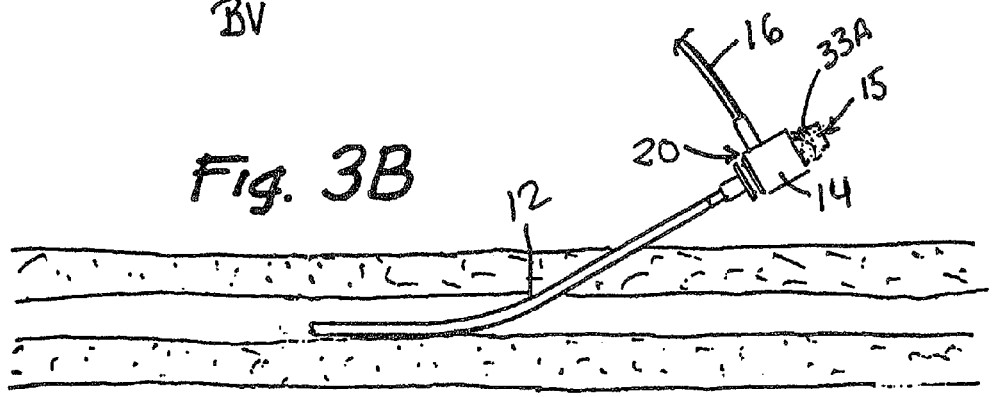
Figure 3C:
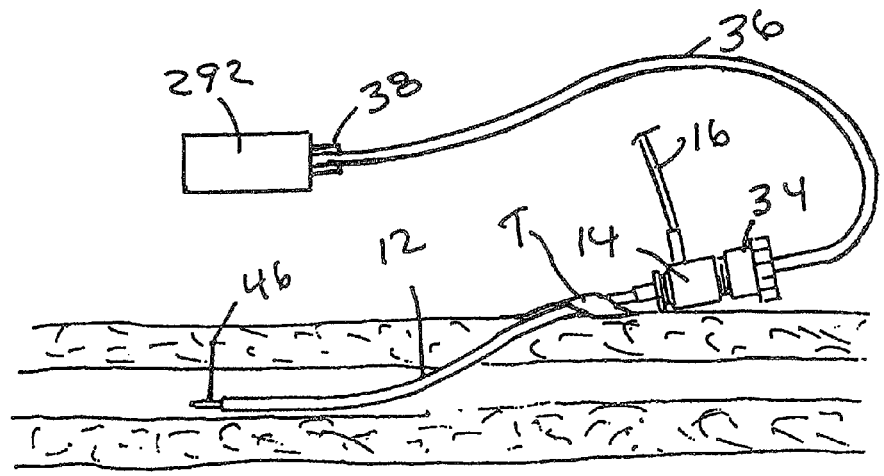

FIGS. 3A-3C show an example of a method for inserting the introducer sheath/temperature probe assembly 10 into a blood vessel, such as a femoral vein. As shown in FIG. 3A, a needle N is initially positioned within the introducer cannula 12 such that the distal end of the needle N protrudes out of the distal end of the cannula 12 and a syringe S containing a small amount of liquid, such as sterile 0.9% NaCl solution, is attached to the proximal end of the needle N. The needle N and cannula 12 are then advanced percutaneously through the skin and underlying tissue while the operator draws back slightly on the plunger of the syringe, until the distal end of the needle enters the lumen of the blood vessel BV and a small amount of blood flows back into the barrel of the syringe S.

Thereafter, as shown in FIG. 3B, the syringe S and needle N are removed, leaving the cannula 12 within the blood vessel BV. The hemostatic valve 20 positioned within the introducer hub 14 prevents blood from backflowing from the out of the proximal opening 15 of the introducer hub 14.

Thereafter, as shown in FIG. 3C, the temperature probe 32 is inserted through the proximal opening 15 of the introducer hub 14, through its hemostatic valve 20, and into the lumen of the introducer cannula 12 to a position where the atraumatic distal tip member 46 protrudes out of the distal end of the introducer cannula 12 but the probe's temperature sensors 40A, 40B are positioned within the cannula 12. The cap member 34 is rotatably advanced onto the proximal end of the cannula hub 14 so that the threaded engagement surfaces 33A, 33B engage one another and the gripping member 35 becomes constricted about the shaft of the probe 32, thereby holding the probe 32 in substantially fixed longitudinal position within the cannula 12. The temperature probe's connector 38 is connected to a controller apparatus 292 which receives and processes temperature signals from the temperature sensors 40A, 40B, as described more fully herebelow.

B. An Endovascular Temperature Control System Incorporating an Introducer Sheath/Temperature Probe Assembly Various types of heat exchange catheters and related apparatus may be used in conjunction with the introducer sheath/temperature probe assembly 10 to alter and/or control the temperature of all or a portion of the body of a human or veterinary patient. Examples of such heat exchange catheters and related apparatus are described in U.S. Pat. Nos. 6,149,676 and 6,149,676 and co-pending U.S. patent application Ser. Nos. 09/138,830, 09/563,946 and 09/707,257, the entireties of which are expressly incorporated herein by reference. FIG. 4 shows one particular endovascular heat exchange system 101 which comprises an introducer sheath/temperature probe assembly 10 of the present invention in combination with a re-usable heater/cooler/control unit 270 and a plurality of disposable components including a heat exchange catheter 260, a heat exchange cassette 276, a saline bag or fluid reservoir 278 and a plurality of fluid flow conduits including a two-way conduit 267 which extends from the heat exchange cassette 276 to the proximal hub 266 of the heat exchange catheter 260. Optionally, the system 101 may further include one or more additional body temperature probes or sensors 265. Such additional body temperature probes or sensor(s) 265 may be desirable in cases where the temperature probe component 30 of the introducer sheath/temperature probe assembly 10 includes only a single temperature sensor 40a or 40b rather than redundant, multiple temperature sensors 40a and 40b, as described hereabove, of if a temperature signal from a different location is desired.

The re-usable heater/cooler/control unit 270 includes an outer housing 284 having a cassette insertion slot 285 into which the heat exchange cassette 276 may be inserted. A heater/cooler 288 such as a thermoelectric plate, a pump driver 290, and a microprocessor controller 292 are positioned within the housing 284. In addition, a manual input unit 294 enables an operator to enter desirable operating parameters into the microprocessor controller 292, for example a pre-selected target body temperature. Each of the electronic devices provided within the control unit 270 communicate through suitable wiring or other connections. Additionally, a wire 36 or other connection (e.g., a wireless connection or fiber optic connection) connects the temperature probe component 30 of the introducer sheath/temperature probe assembly 10 to the microprocessor controller 292, another wire or other connection (e.g., a wireless connection or fiber optic connection) connects a heat transfer fluid temperature and/or flow rate sensor 261 mounted on or in the heat exchange catheter 260 such that a signal indicating the temperature and or flow rate of the heat exchange fluid entering and/or exiting the heat exchange catheter 260 is received by the microprocessor controller 292 and another wire or other connection (e.g., a wireless connection or fiber optic connection) connects the optional additional body temperature sensor(s) 265 (if any) to the microprocessor controller 292. In this manner, the microprocessor controller 292 receives signals or information indicating at least 1) the patient's body temperature as sensed by the introducer sheath/temperature probe assembly 10 and any optional additional body temperature sensors 265, 2) the target body temperature and any other parameters or targets (e.g., maximum rate of cooling or warming) input by the operator through the manual input unit 294, 3) the temperature and/or flow rate of thermal transfer fluid through the heat exchange catheter 260 as sensed by temperature and/or flow rate sensor 261. As those of skill in the art will appreciate, other sensed or operator-input parameters or variables may also be received by the microprocessor controller 292.

Figure 5D:
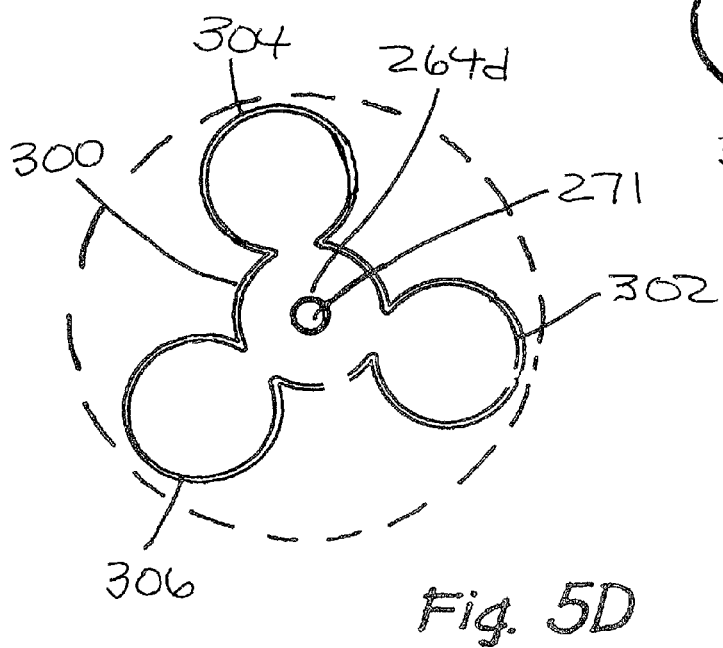
FIG. 5D is a cross-sectional view through line 5D-5D of FIG. 5.

The heat exchange catheter 260 may comprise any suitable type of catheter designed to exchange heat with the patients blood, including those heat exchange catheters described in U.S. Pat. No. 5,486,208 (Ginsburg), PCT International Publication WO OO/10494 (Machold et al.), U.S. Pat. No. 6,264,679 (Keller et al.), PCT International Publication Nos. WO-00/10494 (Radiant Medical, Inc.) and WO 01/58397 (Radiant Medical, Inc.) U.S. Pat. No. 5,411,392 (Saab), U.S. Pat. No. 6,126,684 (Gobin et al.) And U.S. Pat. No. 6,096,068 (Dobak et al.) the entireties of which are expressly incorporated herein by reference. One presently preferred heat exchange catheter 260 for use with this system 101 is shown in FIGS. 4-5D. This particular heat exchange catheter 260 comprises a flexible catheter shaft 264, a proximal hub 266 and a heat exchange balloon 268. A working lumen 271 extends from a proximal port 268 formed in the hub 266, through the catheter shaft 264 and through a distal opening 269 formed in the distal end of the catheter shaft 264. This working lumen 271 may be used as a guidewire lumen, or for passage of various optional apparatus, sensors, probes or other devices 273 (e.g, temperature monitoring probes, pH measuring probes, etc.) and/or for injection/infusion of substances (e.g., radiographic contrast medium, drugs, fluids, etc.). Additionally an inflow lumen 296 extends from an inflow port 297 on the catheter hub 266 into the interior of the heat exchange balloon 268 and an outflow lumen 298 extends from the interior of the heat exchange balloon 268 to an outflow port 299 on the catheter hub 266.

Two way flow conduit 267 has inflow and outflow lumens (not shown) extending therethrough. Bifurcations are formed on both ends of the two way flow conduit 267, as shown in FIG. 4. In this manner, the inflow lumen of the two way flow conduit 267 is connected between the inflow port 297 of catheter hub 266 and an outflow port 275 on the heat exchange cassette 276 and the outflow lumen of the two way flow conduit 267 is connected between the outflow port 299 of catheter hub 266 and an inflow port 277 on the heat exchange cassette 276.

Figure 7:
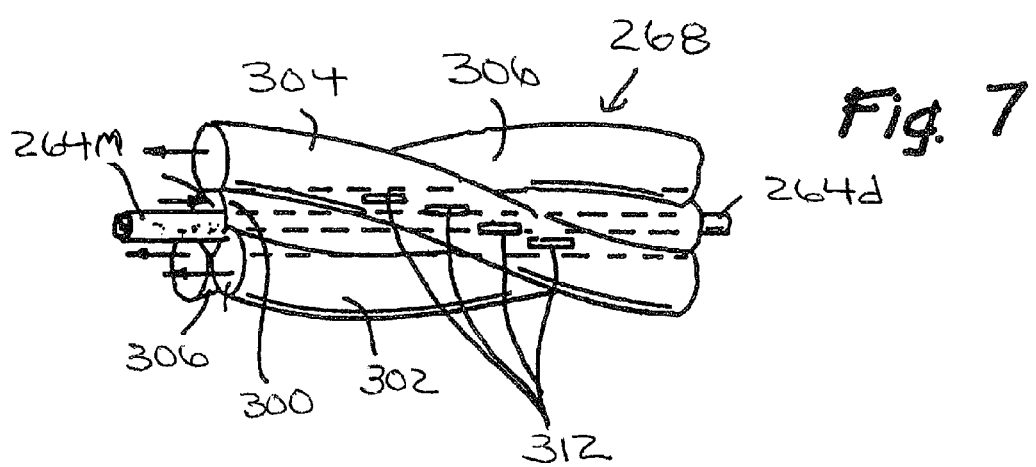
FIG. 7 is an enlarged, perspective view of the portion of the heat exchange catheter within circle 7 of FIG. 5.

As shown in FIGS. 4-7, one example of a heat exchange balloon 268 comprises a multi-lobed structure. The exact number of balloon lobes may vary depending on the particular application for which the heat exchange catheter 260 is being used and/or the size of the blood vessel in which the heat exchange balloon 268 is to be positioned. Preferably the heat exchange balloon 268, when fully inflated, will have a maximum diameter that is at least slightly smaller than the internal diameter of the blood vessel lumen in which it is positioned, thereby allowing blood to flow freely around the inflated heat exchange balloon 268. In the example of FIGS. 4-7, the heat exchange balloon 268 comprises four (4) tubular lobes, a central lobe 300 and three (3) outer lobes 302, 304, 306 that are helically wound about the central lobe 300. As can be seen in FIGS. 5 and 6, the catheter shaft 264 extends into and is joined with the central lobe 300 of the balloon. As may be appreciated particularly from the showings of FIGS. 5A, 5B and 5C and 6, the outflow lumen 298 of the catheter shaft 264 is connected via outflow slots 310 to the interior of the heat exchange balloon 268 such that heat transfer fluid may flow from the interior of the heat exchange balloon 268, through outflow slots 310, through outflow lumen 298, though outflow port 299 of catheter hub 266, through the outflow lumen of two way conduit 267 and into the interior of the heat exchange cassette 276 through its inflow port 277. As shown in FIGS. 5C and 7, a medial catheter shaft 264M which includes a continuation of the inflow lumen 296 and working lumen 271 extends distally through the central lobe 300 of the heat exchange balloon 268 beyond the outflow slots 310 to the distal portion of the balloon where the inflow lumen 296 is connected to the interior of the heat exchange balloon 268 through inflow slots 312. Thus, a pump 293 mounted within the cassette 276 may pump heat transfer fluid from the open inner chamber of the cassette 276, through a convoluted or serpentine flow path defined by a convoluted or serpentine bulkhead or flow director 277 positioned within the cassette 276, through the outflow port 275 of the cassette 276, through the inflow lumen of two way conduit 267, through the inflow port 297 on catheter hub 266, through the inflow lumen 296 of catheter shaft 264 and medial catheter shaft 264M, through inflow slots 312 and into the interior of the heat exchange balloon 268. In this manner heat transfer fluid that has become heated or cooled within the cassette 276 will enter the distal portion of the heat exchange balloon and circulate generally in the proximal direction, exiting from the proximal portion of the heat exchange balloon 268.

C. Automated Control of Patient Temperature Using the Endovascular Temperature Control System and Introducer Sheath/Temperature Probe Assembly In typical use, the heat exchange catheter 260 with its heat exchange balloon 268 in a non-inflated, collapsed state, is percutaneously inserted using a Seldinger technique into a femoral vein of the patient. The heat exchange catheter is then advanced to a position wherein the heat exchange balloon 268 is positioned within the patient's inferior vena cava (IVC). An introducer sheath/temperature probe assembly 10 of the present invention is inserted into the other femoral vein (or any other suitable blood vessel wherein the blood temperature is representative of the body temperature that the operator desires to control or alter. In many applications, the operator will desire to alter or control the patient's core body temperature and, thus, it will be desirable to insert the introducer sheath/temperature probe assembly 10 into a major blood vessel wherein the flowing blood is at or near the patient's core body temperature (e.g., femoral vein, femoral artery, external jugular vein, subclavian vein, etc.).

A bag or vessel 278 containing a suitable heat transfer fluid, such as sterile 0.9% NaCl solution, is attached to the proximal inflow furcation of the two way flow conduit 267, as shown in FIG. 4. The heat transfer fluid is then transferred from the bag or vessel 278 to fill the cassette 276, both lumens of the two way flow conduit 267, the inflow 296 and outflow 298 lumens of the proximal and medial portions of the heat exchange catheter shaft 264, 264M and the lobes 300, 302, 304, 306 of the heat exchange balloon 268. This causes the heat exchange balloon to assume its inflated configuration as shown in FIGS. 4-7. Any large air bubbles are purged such that the heat transfer fluid within the system 101 is substantially free of large air bubbles.

The cassette 276 is inserted into the cassette receiving slot 285 such that the cassette is positioned adjacent to the heater/cooler 288 and the pump driver 290 engages the pump 293.

The connector or plug 38 of the introducer sheath/temperature probe assembly 10 is connected to a corresponding receptacle on the controller 292 of the heating/cooling/control unit 270 and the operator inputs the target body temperature into the input apparatus 294.

The system 101 is then energized and the controller receives the temperature signals from the temperature sensors 40A, 40B within the probe 32 and compares the sensed temperatures. If the difference between the temperatures sensed by the first sensor 40A and the second sensor 40B is greater than the preset allowable difference (e.g., 1 degree difference) the controller will issue a warning signal to the operator and/or will automatically shut down or prevent start up of the pump driver 290, thereby stopping or preventing any heat transfer fluid from being circulated through the heat exchange balloon 268. If, on the other hand, the difference between the temperatures sensed by the first sensor 40A and the second sensor 40B is no more than a preset allowable difference (e.g., 1 degree) the controller will average the two sensed temperatures and that average will be taken as the current measured body temperature to use as the "driver" temperature.

Alternatively, the controller may compare the two signals, and if they are within the predetermined range (e.g. 1 degree C. or 10% or some other appropriate criteria) the controller may ignore one and use the temperature signal from the other as the temperature signal to drive the controller. As yet another alternative, the controller may compare the two signals and select one based on some other criteria, for example if the controller is cooling the patient's body, the controller may select the cooler of the two temperatures as the "driver" temperature to use, and thus avoid overcooling the patient, or if the controller is warming, it may select the warmer of the two as the "driver" temperature signal. If three signals are compared, the controller could also use the median temperature signal as the "driver" signal. These and other similar methods of comparing and using multiple temperature signals are all anticipated by this invention.

The controller 292 then compares this current measured body temperature to the target body temperature that had been entered by the operator and if the current measured body temperature is different from the target temperature, the controller will cause the heater/cooler to either heat or cool the heat transfer fluid within the cassette 276 and/or will adjust the rate at which the driver 290 drives the pump 293 such that the temperature of the heat transfer fluid being circulated through the heat exchange balloon 268 and/or the rate at which the heat transfer fluid is circulated through the heat exchange balloon 268 will cause warming or cooling of the patient's blood until the current measured body temperature reaches the target temperature. The controller 292 may be specifically programmed to minimize or prevent overshoot of the target temperature as described in U.S. Pat. Nos. 5,837,003 (Ginsburg) and 6,149,673 (Ginsburg) and PCT International Patent Publication No. WO-00/10494 (Radiant Medical, Inc.), the entire disclosures of which are expressly incorporated herein by reference. After the target body temperature has been attained, the controller will continuously or periodically redetermine the current measured body temperature and will cause corresponding adjustments in the heater/cooler and or pump driver 290 to maintain the patient's body temperature at or near the target temperature (e.g., target temperature+or −0.5 degrees C.).

While the present invention has been described with reference to the specific embodiments thereof, it should be understood by those skilled in the art that various changes may be made and equivalents may be substituted without departing from the scope of the invention. In addition, many modifications may be made to adapt a particular situation, material, composition of matter, process, process step or steps, while remaining within the scope of the present invention. Accordingly, the scope of the invention should therefore be determined with reference to the appended claims, along with the full range of equivalents to which those claims are entitled.

What is claimed is:

1. An introducer sheath/temperature probe assembly comprising:
   a tubular introducer sheath having a proximal end, an introducer sheath hub on the proximal end, a distal end and a lumen which extends longitudinally therethrough, said introducer sheath being insertable into a blood vessel;
   an elongate temperature probe having a distal end and a proximal end, said temperature measuring probe having a temperature probe hub on the proximal end and being removably insertable, distal end first, into the lumen of the introducer sheath after the introducer sheath has been inserted into a blood vessel, said temperature measuring probe being useable, when inserted into the lumen of the introducer sheath, to sense the temperature of blood flowing through the blood vessel into which the introducer sheath is inserted; and
   a hemostatic valve for preventing blood from backflowing out of the lumen of the introducer sheath, said hemostatic valve being configured to allow the temperature probe to be inserted through the hemostatic valve and into the lumen of the introducer sheath;
   wherein a portion of the temperature probe hub is received within the introducer sheath hub when the temperature probe is inserted into the introducer sheath;
   wherein a first engagement surface is formed on the introducer sheath hub and a second engagement surface is formed on the temperature probe hub, the first engagement surface becoming frictionally engaged with the second engagement surface when the temperature probe is inserted into the lumen of the introducer sheath, thereby deterring unintentional withdrawal of the temperature probe from the introducer sheath; and wherein the first and second engagement surfaces comprise helical threads and the introducer sheath hub and temperature probe hub become engaged to one another by way of said helical threads.

2. An assembly according to claim 1 further comprising a needle that is removably insertable through the lumen of the introducer sheath such that a distal tip of the needle extends out of the distal end of the introducer sheath, the needle and introducer sheath being insertable into the blood vessel, the needle being thereafter removable from the lumen of the introducer sheath and the temperature probe being insertable into the lumen of the introducer sheath following removal of the needle.

3. An assembly according to claim 1 wherein a side port is formed on the hub of the introducer sheath.

4. An assembly according to claim 3 further comprising a side tube having a proximal end and a distal end, the distal end of the side tube being connected to the side port such that fluid may be infused through the side tube, through the side port and through the lumen of the introducer sheath.

5. An assembly according to claim 4 further comprising a stopcock attached to the proximal end of the side tube.

* * * * *